United States Patent
Kotary et al.

(10) Patent No.: US 6,899,280 B2
(45) Date of Patent: May 31, 2005

(54) WICK-BASED DELIVERY SYSTEM WITH WICK HAVING SECTIONS OF VARYING POROSITIES

(75) Inventors: Kara L. Kotary, Racine, WI (US); Padma Prabodh Varanasi, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 98 days.

(21) Appl. No.: 10/266,546

(22) Filed: Oct. 8, 2002

(65) Prior Publication Data

US 2004/0065750 A1 Apr. 8, 2004

(51) Int. Cl.⁷ ............................. A24F 25/00; A61L 9/04
(52) U.S. Cl. ............................. 239/34; 239/44; 239/49; 239/50; 239/57; 239/58; 239/60
(58) Field of Search ............................. 239/34, 44, 45, 239/46, 47, 49, 50, 51, 53, 55, 57, 58, 59, 60

(56) References Cited

U.S. PATENT DOCUMENTS

| | | | | |
|---|---|---|---|---|
| 1,129,897 A | * | 3/1915 | Owen, Jr. ..................... | 239/45 |
| 2,277,377 A | | 3/1942 | Warner ........................ | 299/20 |
| 3,550,853 A | * | 12/1970 | Gray ........................... | 239/44 |
| 3,754,594 A | | 8/1973 | Ferrell ........................ | 165/32 |
| 4,170,262 A | | 10/1979 | Marcus et al. ......... | 165/104.26 |
| 4,419,326 A | | 12/1983 | Santini | |
| 4,449,979 A | | 5/1984 | Holtman ...................... | 604/379 |
| 4,915,301 A | | 4/1990 | Munteanu .................... | 239/45 |
| 5,006,264 A | | 4/1991 | Acuna ......................... | 210/741 |
| 5,094,025 A | * | 3/1992 | Daniels ....................... | 239/136 |
| 5,296,180 A | | 3/1994 | Hayes et al. ................. | 264/44 |
| 5,298,205 A | | 3/1994 | Hayes et al. ................. | 264/414 |
| 5,458,837 A | | 10/1995 | Roberts et al. .......... | 156/89.11 |
| 5,525,374 A | | 6/1996 | Ritland et al. ........... | 427/376.1 |
| 5,647,053 A | | 7/1997 | Schroeder et al. .......... | 392/390 |
| 6,032,488 A | | 3/2000 | Deruyter et al. ............ | 65/17.3 |
| 6,109,539 A | | 8/2000 | Joshi et al. .................. | 239/43 |
| 6,197,709 B1 | | 3/2001 | Tsai et al. ................... | 442/347 |
| 2003/0005620 A1 | * | 1/2003 | Ananth et al. ............... | 43/125 |

* cited by examiner

Primary Examiner—Robin O. Evans

(57) ABSTRACT

A wick-based delivery system includes a container for holding a liquid, and a porous wick, having a first section of a material with a pore size of a predetermined size and a second section of a material of a predetermined pore size that is greater than that of the material of the first section. The porous wick extends through an opening in the container so that when the liquid is added to the container, a lower region of the porous wick is in contact with the liquid, and an upper region of the porous wick is exposed to the ambient air. In one embodiment, at least a portion of the first section and at least a portion of the second section are exposed to the ambient air. In another embodiment, only the second section is exposed to the ambient air.

54 Claims, 5 Drawing Sheets

WICK-BASED DELIVERY SYSTEM WITH WICK HAVING SECTIONS OF VARYING POROSITIES

BACKGROUND OF THE INVENTION

1. Field of the Invention

The present invention relates to a wick-based delivery system for transporting liquids, such as fragrances or insecticides, from a reservoir to a surface exposed to the ambient air.

2. Description of the Related Art

Devices that release vapors into the ambient air are well-known in the art. Generally, the purpose of these devices is to deodorize or disinfect the ambient air, or to distribute toxins into the air to kill or repel unwanted pests, such as mosquitoes.

To achieve the goal of dispensing vapors into the air, a number of methods has been employed. For example, aerosol containers have been used to eject vapors into the air upon the activation of a trigger by the user. Other methods, however, have utilized the evaporative properties of liquids, or other vaporizable materials, to cause vapors with desired properties to be distributed into the ambient air. One such evaporative method utilizes a wick to deliver a vaporizable liquid from a reservoir to a surface exposed to the ambient air. As the liquid reaches the exposed surface, the liquid is vaporized and dispersed into the ambient air. The exposed surface may be either the surface of the wick or the surface of another body in fluid communication with the wick.

In some applications, it is desired that the release rate of the vaporizable liquid be greater when the device is first activated. This initial spike effect is particularly desired when the purpose of the device is to release insecticides or insect repellants into the ambient air. In the case of insect repellant, the benefit of the initial spike effect is that it causes the vaporizable liquid (in particular, the active ingredient of the vaporizable liquid) to be quickly dispersed into the air in an amount sufficient to decrease the number of insects in the surrounding area. Once the optimum level of active ingredient has been released by the initial spike and the ambient air of the operating area is sufficiently saturated, however, it is preferable that the release rate of the vaporizable liquid be decreased. This decrease in the release rate is preferred because the optimum saturation level of the ambient air has already been achieved, and the release rate of the vaporizable liquid after the initial period need only be sufficient to maintain that optimum level.

Accordingly, when an insect control device is first activated, it is preferred that the device initially release a relatively high amount of the vaporizable liquid into the ambient air, and then, after that initial spike, the release rate of the device should be maintained at a lower level.

An example of a wick-based, controlled release device is described in U.S. Pat. No. 4,915,301. This patent discloses a bottle for dispensing a liquid in vapor phase. More specifically, the bottle contains a liquid and that liquid is absorbed by a wick and conveyed to a porous body. The liquid then spreads through the porous body and reaches a microporous membrane which permits the liquid to be discharged as a vapor into the atmosphere. The membrane serves to enable emission of vapors of the liquid, while preventing passage of the liquid itself. Accordingly, the exposed surface of this device consists solely of a microporous membrane. Although this membrane helps prevent spillage of the liquid through the wick, it cannot provide an initial spike effect followed by a lower, steady release rate.

U.S. Pat. No. 6,109,539 discloses an inverted aromatic substance dispenser that can be comprised of porous plugs with different porosities. However, this dispenser also has a material of only one pore size exposed to the ambient air and, therefore, this dispenser cannot provide an initial spike effect followed by a lower, steady release rate.

Another wicking device is disclosed in U.S. Pat. No. 2,277,377. This patent discloses a device that comprises a cotton wick surrounded by a sheath made of bentonite, a clay-like substance. The device is inserted into a reservoir to lift liquid from the reservoir to the surface of the bentonite sheath. Again, however, the design of this device is such that material of only one pore size is exposed to the ambient air and, therefore, this dispenser cannot provide an initial spike effect followed by a lower, steady release rate.

SUMMARY OF THE INVENTION

In one aspect, the present invention provides a device comprising: (a) a container for holding a liquid, and (b) a porous wick comprised of sections of varying pore size. In particular, the porous wick is comprised of a section of small pores and a section with larger pores. The porous wick is positioned so that a lower region of the wick will be in contact with the liquid and an upper region of the wick is exposed to the ambient air. In addition, at least a portion of the first section and at least a portion of the second section are exposed to the ambient air.

In another aspect, the present invention provides a device comprising: (a) a container for holding a liquid, and (b) a porous wick comprised of sections of varying pore size. In particular, the porous wick is comprised of a section of small pores and a section with larger pores. The porous wick extends through an opening at the top surface of the container so that the opening is substantially sealed by the wick. The wick is positioned so that a lower region of the wick will be in contact with the liquid and an upper region of the wick is exposed to the ambient air. In addition, at least a portion of the first section and at least a portion of the second section are exposed to the ambient air.

In yet another aspect, the present invention provides a device comprising: (a) a liquid, (b) a container for holding the liquid, and (c) a porous wick comprised of sections of varying pore size. In particular, the porous wick is comprised of a section of small pores and a section with larger pores. The porous wick is positioned so that a lower region of the wick is in contact with the liquid and an upper region of the wick is exposed to the ambient air. In addition, at least a portion of the first section and at least a portion of the second section are exposed to the ambient air.

In still another aspect, the present invention provides a device comprising: (a) a liquid, (b) a container for holding the liquid, wherein the container has an opening at a top surface, and (c) a porous wick comprised of sections of varying pore size. In particular, the porous wick is comprised of a section of small pores and a section with larger pores. The porous wick extends through the opening of the container, with a lower region of the porous wick in contact with the liquid and an upper region of the porous wick exposed to the ambient air. The opening in the container is also substantially sealed by the porous wick. In addition, at least a portion of the first section and at least a portion of the second section are exposed to the ambient air.

In a further aspect, the present invention provides a device comprising: (a) a container for holding a liquid, the container including an opening therein, and (b) a porous wick having a first section comprised of a material with a predetermined pore size and a second section comprised of a material with a predetermined pore size that is greater than that of the first section. The wick is positioned so that a lower region of the wick will be in contact with the liquid to be held by the container and an upper region of the wick is exposed to the ambient air. The opening in the container is substantially sealed by the wick. In addition, only the second section of the wick is exposed to the ambient air.

A better understanding of these and other features and advantages of the invention may be had by reference to the drawings and to the accompanying description, in which preferred embodiments of the invention are illustrated and described.

BRIEF DESCRIPTION OF THE DRAWINGS

Throughout the figures, like or corresponding reference numerals have been used for like or corresponding parts.

DETAILED DESCRIPTION OF THE INVENTION

The present invention relates to a wick-based delivery system for transporting a liquid from a reservoir to a surface that is exposed to the ambient air. In its simplest form, the invention comprises a device that includes a container for holding a liquid, and a two-section wick for transporting the liquid from the container to an upper surface of the wick.

Figure 1:
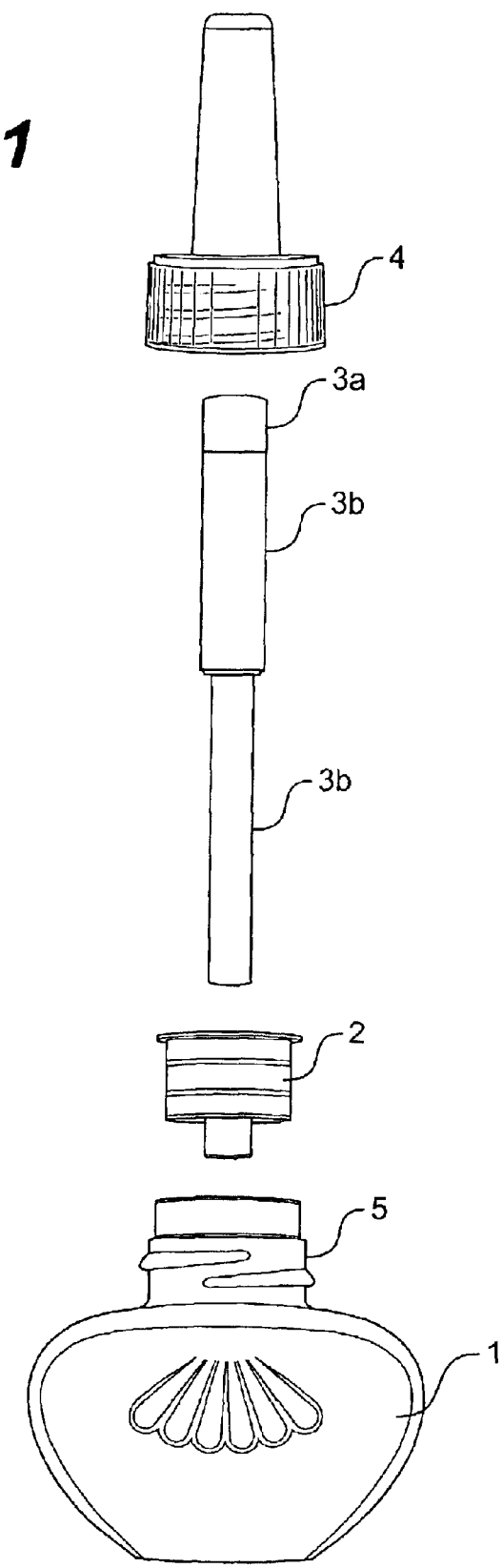
FIG. 1 shows an exploded view of a wick-based delivery system according to a preferred embodiment of the present invention.
Figure 2A:
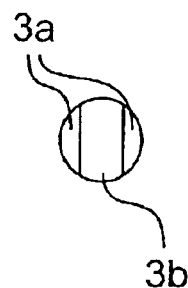
FIG. 2A shows a top view of a wick according to another preferred embodiment of the present invention.
Figure 2B:
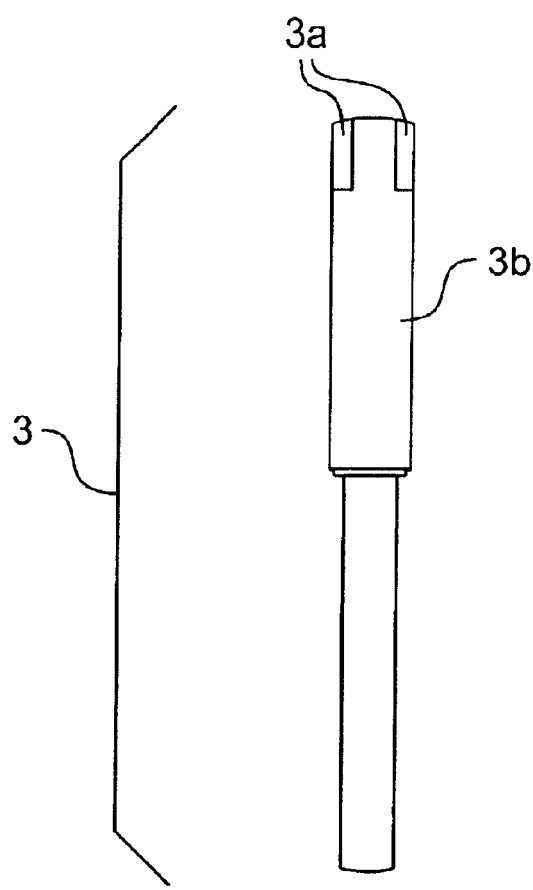
FIG. 2B shows a side view of the wick shown in FIG. 2A.

The container can be formed in a variety of shapes. In FIG. 1, for example, the container is a bottle 1 of conventional shape. A wick 3 is shaped so that it fits snugly into a neck 5 of the bottle 1. The wick 3 is long enough so that its bottom surfaces come into contact with the liquid in the bottle 1 and its top surfaces are exposed to the ambient air. (The level of the liquid is not shown in the bottle 1.) It is preferable to use a neck closure 2, such as that shown in FIG. 1, to hold the wick 3 in place and to prevent leakage around the neck 5 of the bottle 1. The fit between the neck closure 2 and the bottle 1 is tight enough to prevent leakage of the liquid from the bottle 1. Likewise, the fit between the neck closure 2 and the wick 3 is sufficiently tight to prevent leakage of the liquid from the bottle 1.

The neck closure 2 or neck 5 of the bottle 1 may be formed with a small hole (e.g., a vent-hole) to help counter the effects of a vacuum that can form in the head-space of the bottle 1. The wick 3 transports the liquid to the surface of the wick 3 by a principle called capillary action. In particular, the wick material contains numerous pores, and these pores act as capillaries, which cause the liquid to be drawn into them. As the liquid is drawn from the bottle and transported up the porous wick 3, a vacuum is created in the head-space of the bottle 1. The formation of a vacuum in the head-space of the bottle 1 decreases the rate that the liquid is wicked from the reservoir to the surface. Of course, this decrease in the wicking rate translates directly into a decrease in the release rate of the liquid to the ambient air. Accordingly, in order to combat the formation of the vacuum in the head-space, it is often preferable to form a vent-hole in the vicinity of the head-space of the bottle 1.

In addition, the neck 5 of the bottle 1 can be shaped so that a cover 4 can be securely fastened over the wick 3 and neck closure 2. For example, the outer neck 5 of the bottle 1 may be threaded so that a cover 4 can be screwed on top of the bottle 1 when the device is not in use.

The bottle 1 and the neck closure 2 can be made of any suitable material that is leakproof. Of course, the size of the opening in the bottle 1 and the size of the neck closure 2 are dependent upon each other and upon the size of the wick 3 that is to be used with the device.

The wick 3 can be made of a variety of materials. It is preferable that the wick 3 be rigid enough to provide minimal contact area with the surface that the wick 3 comes in contact with. Polymeric wicks, for example, have been found to be effective for these purposes. In particular, wicks composed of ultra high molecular weight, high density polyethylene (HDPE) have been found to be suitable. Such wicks are generally comprised of blends of HDPE in particle form, and the blends are developed to meet the target pore characteristics of the wick 3.

Preferably, the solubility parameter of the polymer is significantly different from that of any of the components contained in the liquid. This prevents the wick 3 from swelling, or other changes, which can lead to a change in the pore size and porosity of the wick 3. If the pore size or porosity of the wick 3 is altered, the release rate of the vaporizable liquid into the ambient air would also be affected.

As described above, it is often desired that the device exhibit an initial spike in the release rate of the vaporizable liquid when the device is first activated. More specifically, when an insect repelling device is activated, an initial spike in the release rate of the active ingredient (e.g., insecticide) is desired in order to quickly disperse into the air a sufficient amount of the active ingredient to effectively decrease the number of insects in the surrounding area. Once an optimum level of active ingredient is present in the ambient air of the operating area, however, the release rate of the active ingredient should be decreased to an amount that is sufficient to maintain that optimum level. By having two sections of varying pore size exposed to the ambient air at the same time, it is possible to achieve an initial spike effect.

In particular, the initial spike effect is achieved by having a wick 3 that is comprised of at least two sections. A first section 3a is made of a material that has a particular pore size, while the second section 3b is made of a material that has a pore size that is greater than that of the material of the first section. Both sections of the wick are exposed to the ambient air.

In FIG. 1, the cylindrical shape of the large pore section 3b is also narrowed at its lower portion. The pore size of the lower portion of large pore section 3b, however, does not change with this change in diameter. Importantly, this change in shape is not required for achieving the initial spike effect. Instead, this variation in shape can be useful in that it both increases the amount of the surface area exposed to the ambient air and aids in forming a tighter seal at the neck 5 area of the bottle 1, thus helping to prevent spilling or leaking of the liquid from the bottle 1.

Generally speaking, the equilibrium rise within a wick increases as pore size decreases, while the rate of wicking decreases as the pore size decreases. Accordingly, a wick 3 with a small pore size will transport a liquid more slowly, but the capillary action is greater. Because equilibrium rise within a wick 3 increases as pore size decreases, the section of small pores 3a will get saturated with the liquid, and the large pore section 3b will not, when the device is not activated.

When the device is activated, the release of the liquid occurs from all exposed surfaces of the wick 3, which includes a surface of the small pore section 3a and a surface of the large pore section 3b. However, when the liquid in the small pore section 3a is depleted, the small size of the pores in that section delays the wicking of additional liquid into the small pore section 3a. Therefore, shortly after the device is activated, the small pore section 3a no longer contributes to the release of the liquid into the ambient.

When the device is deactivated, the strong capillary action of the small pore size section 3a slowly causes the area of the small pore section 3a to be re-saturated with the liquid. In this manner, the device is able to provide the initial spike effect as long as there is sufficient liquid remaining in the system and enough time for the small pore size section 3a to replenish itself between cycles of use.

Figure 3A:
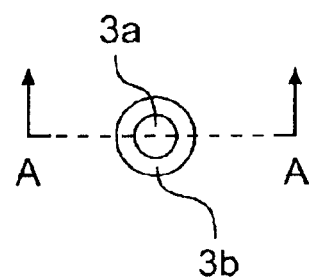
FIG. 3A shows a top view of a wick according to yet another preferred embodiment of the present invention.
Figure 3B:
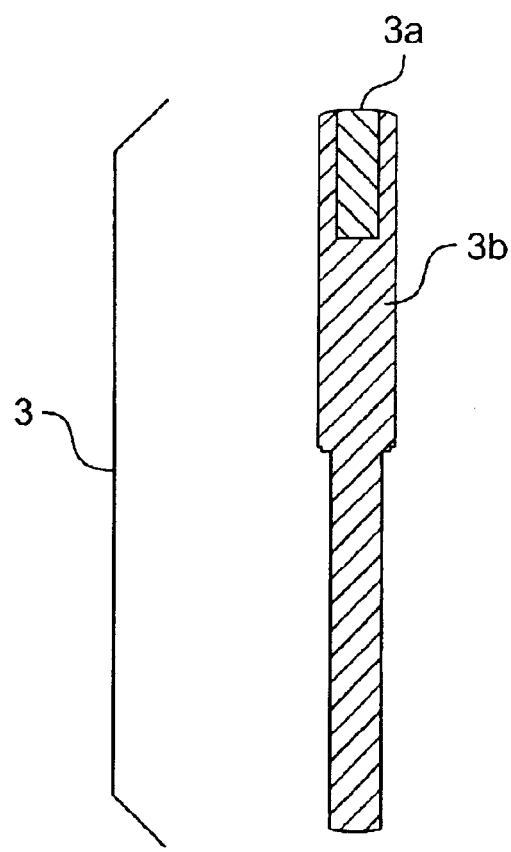
FIG. 3B is a cross-sectional view taken along section line A—A in FIG. 3A.
Figure 4A:
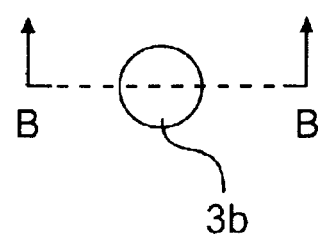
FIG. 4A shows a top view of a wick according to still another preferred embodiment of the present invention.
Figure 4B:
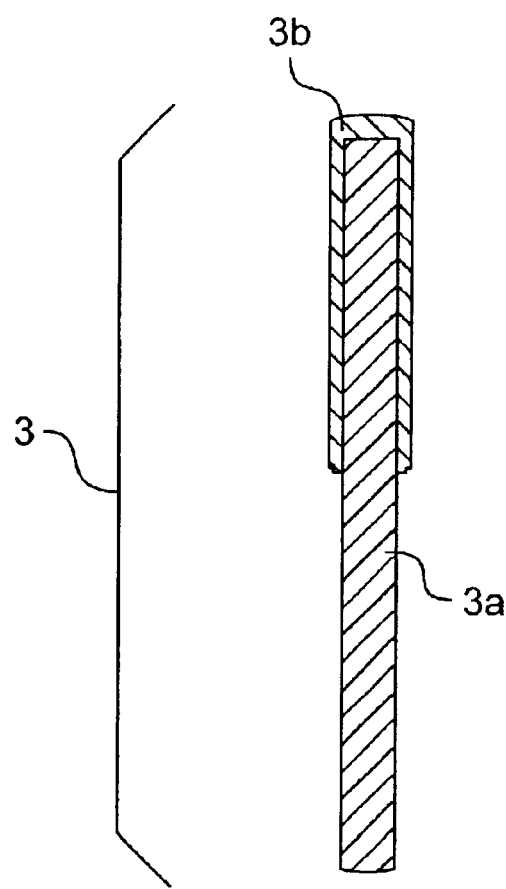
FIG. 4B is a cross-sectional view taken along section line B—B in FIG. 4A.
Figure 5:
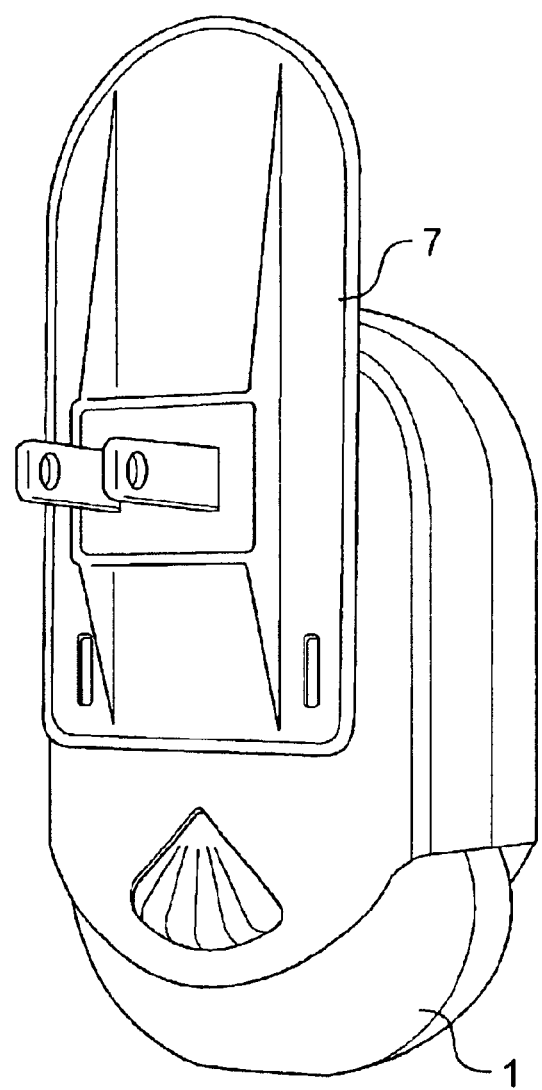
FIG. 5 shows a view of a wick-based delivery system according to the present invention being utilized in conjunction with an optional electric plug-in heater.

Accordingly, when an insect control device of this invention is first activated, the liquid (active ingredient) is initially released into the ambient air from both exposed wick sections 3a and 3b, and then, after the small pore section 3a is depleted, the release rate of the device is limited to the rate at which the larger pore section 3b works to disperse the vaporized liquid to the ambient air.

Of course, the above-described initial spike effect can be obtained with wicks 3 of many different shapes and forms. FIG. 1, for example shows a wick 3 that has a small pore section 3*a* of a cylindrical shape stacked upon a larger pore section 3*b*, also of a cylindrical shape. FIGS. 2A, 2B, 3A, and 3B show other possible configurations, which are discussed in more detail below. As long as the exposed surface of the wick 3 contains a section with a sufficiently small pore size and a section with a sufficiently large pore size, the small pore size section will deplete itself and cause the initial spike effect described above.

The preferred pore size of the small pore size section 3*a* and large pore size section 3*b* will vary depending upon the composition of the liquid to be dispersed into the air. However, we have found that it is preferable that the ratio of the large pore size to that of the small pore size is above about two, and more preferably above about five, and even more preferably above ten, for any given viscosity. In other words, if the large pore size is around ten microns, the small pore size is most preferably below one micron. If the large pore size is about one hundred microns, the small pore size is most preferably below ten microns. It should be noted that any difference in pore size will produce an initial spike effect. In the case of a smaller ratio, however, the spike effect will also be smaller, and, therefore, less effective.

The mean pore size of the wick 3 can be determined by any standard test for determining porosity and pore size distribution. For example, mercury porosimetry is a method that gives information on porosity and pore size distribution for rigid wicks. It is based on the measurement of differential increments in the amount of mercury intruded into the wick as a function of increasing applied pressure.

We also contemplate that there may be multiple sections of small pore size 3*a* exposed to the ambient air. An example of a wick 3 having multiple sections of small pore size 3*a* is shown in FIGS. 2A and 2B. In fact, it may be preferable to use several sections of small pore size 3*a* in order to achieve a more uniform initial spike effect and/or to minimize leakage from the wick 3 as described above. In addition, it is possible that the small pore section 3*a* may be arranged so that it extends into the bottle 1 and is itself in contact with the liquid in the bottle 1.

FIGS. 3A and 3B show yet another possible wick configuration for achieving a spike effect. In this example, the small pore size section 3*a* is arranged concentrically within the larger pore size section 3*b*.

Another advantage in using a wick 3 that has a section of small pore size is that the likelihood of liquid spilling or leaking through the wick itself can be decreased. In particular, it is less likely that liquid will escape from the small pore section 3*a* and, therefore, it is possible to design the wick so that the small pore section 3*a* is located in the area where the liquid is most likely to spill from. As indicated above, it is not necessary that the small pore section 3*a* be positioned as shown in FIG. 1. Instead, the small pore section 3*a* could be placed, for example, on the side to which the device is most likely to tip (either in use by the consumer or in manufacture or shipping by the producer). Therefore, the small pore section 3*a* could be placed where it is most likely to aid in the prevention of spilling or leaking of the liquid through the wick 3.

For example, as shown in FIGS. 4A and 4B, it is possible to provide a wick 3 with an outer layer that is made up of a material with larger pore sizes. In FIGS. 4A and 4B, the large pore outer section 3*b* completely surrounds the exposed portion of the wick 3. The small pore size section 3*a* extends into the bottle 1 and is in contact with the liquid. In this manner, the smaller pores of the inner portion 3*a* of the wick 3 prevent leakage, while the larger pores of the outer portion 3*b* provide a maximum release rate of the vaporizable liquid off the surface of the wick 3 that is exposed to the ambient air. It should be noted, however, that the large pore section 3*b* need not completely surround the upper region of the small pore section 3*a* as shown in FIGS. 4A and 4B in order to provide the benefits of our invention.

The present wick-based delivery system can also be combined with an electric heater to facilitate the release of the vaporizable material into the ambient air. In fact, when we speak of activation (and deactivation), generally what is meant is that the heater, or other such mechanism, is turned on or off. Of course, the device may operate without such an aid and the periods of activation and deactivation may be achieved by simply exposing or restricting the exposure of the wick to the ambient air, such as by the removal or addition of a cover over the wick. FIG. 3 shows an example of the type of electric heater 7 that may be used for this purpose. In addition, U.S. Pat. No. 5,647,053 describes such an electric plug-in heater and is incorporated herein by reference.

Other means for facilitating the use of the wick-based delivery system of the present invention are also envisioned. For example, the invention may also be combined with a battery powered fan. Although not required, it is preferable that the wick-based delivery system of the invention be combined with the electric plug-in heater or fan in a removable manner. For example, the wick-based delivery system of the invention may constructed so that the bottle 1 can be combined with an electric plug-in heater 7, for example, in a snap-and-fit manner as shown in FIG. 3.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

INDUSTRIAL APPLICABILITY

The present invention provides a device useful as a means to transport a liquid from a reservoir to a surface that is exposed to the ambient air. We envision that this device preferably can be used, for example, to dispense fragrances, insecticides, and any other vaporizable materials into the ambient air to freshen or deodorize the air or to exterminate airborne pests.

We claim:

1. A device comprising:
   a container for holding a liquid; and
   a porous wick having a first section comprised of a material with a predetermined pore size and a second section comprised of a material with a predetermined pore size that is greater than that of the material of the first section, positioned so that at least a portion of the second section of the wick will be in contact with the liquid to be held by the container and an upper region of the wick is exposed to the ambient air,
   wherein at least a portion of the first section and at least a portion of the second section are exposed to the ambient air.

2. The device of claim 1, wherein the ratio of the pore size of the second section to that of the first section is greater than about two.

3. The device of claim 1, wherein the ratio of the pore size of the second section to that of the first section is greater than about five.

4. The device of claim 1, wherein the ratio of the pore size of the second section to that of the first section is greater than about ten.

5. The device of claim 1, wherein the wick is comprised of high density polyethylene.

6. The device of claim 1, further comprising a plurality of at least one of the first section and the second section.

7. The device of claim 1, wherein the first section is formed on top of the second section.

8. The device of claim 7, wherein each of the first section and the second section is cylindrical in shape.

9. The device of claim 1, wherein the first section is formed concentrically within the second section.

10. The device of claim 1, further comprising a heater for heating liquid drawn through the wick.

11. The device of claim 10, wherein the heater is an electric plug-in heater.

12. A device comprising:
    a container for holding a liquid, the container having an opening at a top surface of the container; and
    a porous wick, the wick extending through the opening in the container such that a lower region of the wick will be in contact with the liquid to be held by the container and an upper region of the wick is exposed to the ambient air, wherein the opening in the container is substantially sealed by the wick,
    the wick having a first section comprised of a material with a predetermined pore size and a second section comprised of a material with a predetermined pore size that is greater than that of the material of the first section, wherein at least a portion of the first section and at least a portion of the second section are exposed to the ambient air, and at least a portion of the second section will be in contact with the liquid to be held by the container.

13. The device of claim 12, further comprising a neck closure having a hole, wherein the neck closure fits tightly into the opening of the container and the wick fits tightly into the hole of the neck closure, such that the opening of the container is substantially sealed by the neck closure and the wick.

14. The device of claim 12, wherein the ratio of the pore size of the second section to that of the first section is greater than about two.

15. The device of claim 12, wherein the ratio of the pore size of the second section to that of the first section is greater than about five.

16. The device of claim 12, wherein the ratio of the pore size of the second section to that of the first section is greater than about ten.

17. The device of claim 12, wherein the wick is comprised of high density polyethylene.

18. The device of claim 12, further comprising a plurality of at least one of the first section and the second section.

19. The device of claim 12, wherein the first section is formed on top of the second section.

20. The device of claim 19, wherein each of the first section and the second section is cylindrical in shape.

21. The device of claim 12, wherein the first section is formed concentrically within the second section.

22. The device of claim 12, further comprising a heater for heating liquid drawn through the wick.

23. The device of claim 22, wherein the heater is an electric plug-in heater.

24. A device comprising:
    a liquid;
    a container for holding the liquid; and
    a porous wick having a first section comprised of a material with a predetermined pore size and a second section comprised of a material with a predetermined pore size that is greater than that of the material of the first section, positioned so that at least a portion of the second section of the wick is in contact with the liquid held by the container and an upper region of the wick is exposed to the ambient air,
    wherein at least a portion of the first section and at least a portion of the second section are exposed to the ambient air.

25. The device of claim 24, wherein the ratio of the pore size of the second section to that of the first section is greater than about two.

26. The device of claim 24, wherein the ratio of the pore size of the second section to that of the first section is greater than about five.

27. The device of claim 24, wherein the ratio of the pore size of the second section to that of the first section is greater than about ten.

28. The device of claim 24, wherein the wick is comprised of high density polyethylene.

29. The device of claim 24, further comprising a plurality of at least one of the first section and the second section.

30. The device of claim 24, wherein the first section is formed on top of the second section.

31. The device of claim 30, wherein each of the first section and the second section is cylindrical in shape.

32. The device of claim 24, wherein the first section is formed concentrically within the second section.

33. The device of claim 24, further comprising a heater for heating liquid drawn through the wick.

34. The device of claim 33, wherein the heater is an electric plug-in heater.

35. A device comprising:
   a liquid;
   a container for holding the liquid, the container having an opening at a top surface of the container; and
   a porous wick, the wick extending through the opening in the container such that a lower region of the wick is in contact with the liquid held by the container and an upper region of the wick is exposed to the ambient air, wherein the opening in the container is substantially sealed by the wick,
   the wick having a first section comprised of a material with a predetermined pore size and a second section comprised of a material with a predetermined pore size that is greater than that of the material of the first section, wherein at least a portion of the first section and at least a portion of the second section are exposed to the ambient air, and a least a portion of the second section is in contact with the liquid held by the container.

36. The device of claim 35, further comprising a neck closure having a hole, wherein the neck closure fits tightly into the opening of the container and the wick fits tightly into the hole of the neck closure, such that the opening of the container is substantially sealed by the neck closure and the wick.

37. The device of claim 35, wherein the ratio of the pore size of the second section to that of the first section is greater than about two.

38. The device of claim 35, wherein the ratio of the pore size of the second section to that of the first section is greater than about five.

39. The device of claim 35, wherein the ratio of the pore size of the second section to that of the first section is greater than about ten.

40. The device of claim 35, wherein the wick is comprised of high density polyethylene.

41. The device of claim 35, further comprising a plurality of at least one of the first section and the second section.

42. The device of claim 35, wherein the first section is formed on top of the second section.

43. The device of claim 42, wherein each of the first section and the second section is cylindrical in shape.

44. The device of claim 35, wherein the first section is formed concentrically within the second section.

45. The device of claim 35, further comprising a heater for heating liquid drawn through the wick.

46. The device of claim 45, wherein the heater is an electric plug-in heater.

47. A device comprising:
   a container for holding a liquid, the container including an opening therein; and
   a porous wick having a first section comprised of a material with a predetermined pore size and a second section comprised of a material with a predetermined pore size that is greater than that of the first section, positioned so that a lower region of the wick will be in contact with the liquid to be held by the container and an upper region of the wick is exposed to the ambient air,
   wherein the opening in the container is substantially sealed by the wick, and only the second section of the wick is exposed to the ambient air.

48. The device of claim 47, further comprising a neck closure having a hole, wherein the neck closure fits tightly into the opening of the container and the wick fits tightly into the hole of the neck closure, such that the opening of the container is substantially sealed by the neck closure and the wick.

49. The device of claim 47, wherein the ratio of the pore size of the second section to that of the first section is greater than about two.

50. The device of claim 47, wherein the ratio of the pore size of the second section to that of the first section is greater than about five.

51. The device of claim 47, wherein the ratio of the pore size of the second section to that of the first section is greater than about ten.

52. The device of claim 47, wherein the wick is comprised of high density polyethylene.

53. The device of claim 47, further comprising a heater for heating liquid drawn through the wick.

54. The device of claim 53, wherein the heater is an electric plug-in heater.

* * * * *